United States Patent
Schmidt et al.

(10) Patent No.: US 7,195,810 B1
(45) Date of Patent: Mar. 27, 2007

(54) AIR-LAID ABSORBENT SHEET WITH SINUATE EMBOSS

(75) Inventors: Bradley G. Schmidt, Green Bay, WI (US); Jennifer N. Wergin, Green Bay, WI (US); Barbara V. Buman, Oneida, WI (US); Michael P. Bouchette, Sherwood, WI (US)

(73) Assignee: Fort James Corporation, Atlanta, GA (US)

( * ) Notice: Subject to any disclaimer, the term of this patent is extended or adjusted under 35 U.S.C. 154(b) by 0 days.

(21) Appl. No.: 09/553,928

(22) Filed: Apr. 21, 2000

Related U.S. Application Data

(60) Provisional application No. 60/131,144, filed on Apr. 27, 1999.

(51) Int. Cl.
```
B32B 3/00      (2006.01)
B32B 3/28      (2006.01)
B32B 3/30      (2006.01)
A61F 13/15     (2006.01)
A61F 13/20     (2006.01)
```
(52) U.S. Cl. ............... 428/156; 428/171; 428/172; 428/167; 428/153; 162/109; 162/113; 162/157.1; 162/157.6; 604/385.01; 604/385.23; 604/379; 604/380; 604/370; 604/371; 604/365; 604/367; 604/374; 604/378; 604/358

(58) Field of Classification Search ........ 604/378–380, 604/385.01, 358, 374, 385.23, 365, 367, 604/371, 370; 428/156, 171, 167, 152, 153, 428/154, 172, 166; 162/109, 111, 113, 157.1, 162/157.6

See application file for complete search history.

(56) References Cited

U.S. PATENT DOCUMENTS

| | | | |
|---|---|---|---|
| 728,828 A | 5/1903 | Arkell | |
| 1,808,536 A | 6/1931 | Fisk | |
| 1,820,388 A | 8/1931 | Youngchild et al. | |
| 2,788,003 A | 4/1957 | Morin | 128/284 |
| D186,259 S | 9/1959 | Howell | D92/1 |
| 2,943,560 A | 7/1960 | Wrob et al. | 101/23 |
| 3,065,751 A | 11/1962 | Gobbo et al. | 128/287 |
| 3,347,162 A | 10/1967 | Breznell et al. | 101/376 |
| 3,425,347 A | 2/1969 | Nard | 101/376 |
| 3,672,950 A | 6/1972 | Murphy et al. | 161/129 |
| 3,738,905 A * | 6/1973 | Thomas | 428/154 |
| 3,768,118 A * | 10/1973 | Ruffo et al. | 264/511 |
| 3,860,002 A * | 1/1975 | Kolbach | 128/284 |
| 3,879,257 A * | 4/1975 | Gentile et al. | 162/112 |
| 3,881,490 A | 5/1975 | Whitehead et al. | 128/287 |
| 3,953,638 A * | 4/1976 | Kemp | 428/154 |
| RE29,789 E | 10/1978 | Kolbach | 128/284 |

(Continued)

FOREIGN PATENT DOCUMENTS

EP          810078 A1 * 12/1997

*Primary Examiner*—Alicia Chevalier
*Assistant Examiner*—Catherine A. Simone
(74) *Attorney, Agent, or Firm*—Joel T. Charlton

(57) ABSTRACT

An absorbent sheet made from an air-laid fiber web includes a functional emboss pattern of a continuous (wave-like) shape extending in the machine direction of the sheet. The emboss pattern defines a plurality of compressed regions operative to preferentially convey sorbed liquid away from the point of insult to prevent product failure. The sheet is particularly useful as absorbent core material within a multi-layer absorbent pad. In a further aspect of the invention, there is provided a method of making absorbent sheet utilizing an emboss roll provided with radially projecting circumferential sinuate bosses.

39 Claims, 4 Drawing Sheets

U.S. PATENT DOCUMENTS

| | | | | |
|---|---|---|---|---|
| 4,154,883 A | 5/1979 | Elias | ............................ | 428/171 |
| 4,339,088 A | 7/1982 | Niedermeyer | ................... | 242/1 |
| 4,437,917 A | 3/1984 | Tao et al. | .................... | 156/296 |
| 4,476,078 A | 10/1984 | Tao | ............................. | 264/119 |
| 4,482,308 A | 11/1984 | Johnson | ...................... | 425/83.1 |
| 4,483,728 A | 11/1984 | Bauernfeind | ................. | 156/209 |
| 4,544,596 A * | 10/1985 | Holtman | ...................... | 428/171 |
| 4,612,231 A | 9/1986 | Bouchette et al. | ........... | 428/167 |
| 4,634,484 A | 1/1987 | Wagner | ........................ | 156/219 |
| 4,917,903 A | 4/1990 | Mente | ....................... | 425/174.4 |
| 5,128,082 A | 7/1992 | Makoui | ........................ | 264/112 |
| 5,173,351 A * | 12/1992 | Ruppel et al. | .............. | 428/1.74 |
| 5,269,983 A | 12/1993 | Schulz | ......................... | 364/25 |
| D352,833 S | 11/1994 | Schulz | ......................... | D5/53 |
| 5,429,630 A | 7/1995 | Beal et al. | ................. | 604/385.1 |
| 5,529,563 A | 6/1996 | Veith et al. | ................... | 493/395 |
| 5,591,149 A | 1/1997 | Cree et al. | ................... | 604/378 |
| 5,759,473 A | 6/1998 | Minke et al. | ................ | 264/400 |
| 5,861,081 A | 1/1999 | Bredendick et al. | ......... | 162/114 |
| 5,865,824 A * | 2/1999 | Chen et al. | ................... | 604/378 |
| 5,874,156 A | 2/1999 | Schulz | ......................... | 428/156 |
| 5,895,380 A * | 4/1999 | Turi et al. | .................... | 604/383 |
| 6,312,416 B1 * | 11/2001 | Brisebois et al. | ......... | 604/385.1 |

* cited by examiner

AIR-LAID ABSORBENT SHEET WITH SINUATE EMBOSS

This application claims the benefit of U.S. Provisional Application Ser. No. 60/131,144, filed Apr. 27, 1999.

TECHNICAL FIELD

The present invention relates generally to air-laid absorbent sheet and more particularly to an air-laid absorbent sheet provided with a continuous sinuate (wave-like) functional emboss pattern in the machine direction operative to enhance fluid distribution in the product.

BACKGROUND ART

Embossing cellulosic absorbent sheet products to alter their mechanical or tactile characteristics is well known. There is shown in U.S. Pat. No. 1,808,536 to Fisk a method and apparatus for embossing paper tissue and towels using an embossing roll with a wave-like pattern. The pattern on the roll has a relief height of 0.075 or more above the general surface of the roll (col. 2, lines 69–75). The method is reported to be particularly suitable for wet creped products, prior to the web contacting drier rolls.

There is shown in U.S. Pat. No. Des. 186,259 to Howell a puffed textile fabric with a wave-like design. So also, U.S. Pat. No. 728,828 to Arkell shows a bi-directional wave pattern imposed on a paper structure.

U.S. Pat. No. 3,672,950 of Murphy et al. is directed to adhesively laminated creped products wherein the plies are bonded in superposed relation by an adhesive disposed between the webs (col. 2, lines 15–25). The adhesive may be applied in a wave-like pattern in the machine direction (FIGS. 1,4), while the webs may be embossed with a great number of pin-like embossments. The embossments extend from the body of the web for a predetermined distance as required to keep the two webs suitably spaced, the two webs being superposed with the protuberances of each web facing the other web (col. 4, lines 29–37; col. 6, line 74–col. 7, line 1).

In U.S. Pat. No. 4,339,088 to Niedermeyer there is described an embossing method to avoid nesting in convolutely wound rolls wherein the repeat length is at least as great as the circumference of the roll. In Example I, a sine wave pattern of embossment nodes is laid out in the machine direction (col. 4, lines 5–35).

U.S. Pat. No. 5,861,081 of Bredendick describes a single ply-paper towel with a plurality of infundibulate bosses formed therethrough. The towel has areas of light bosses and heavy boss perforations which form islands of heavy boss perforations surrounded by intersecting bands of light bosses (col. 3, lines 33–38).

Air-laid absorbent sheet products are likewise well-known. U.S. Pat. No. 4,437,917 to Tao et al. describes a method of increasing the caliper and bulk of air-laid dry fibrous webs. The method generally includes measuring the caliper downstream of the bond curing drier and adjusting drier conditions on the basis of the caliper measurements.

U.S. Pat. No. 4,482,308 to Johnson teaches an apparatus for depositing dry fibers on a foraminous support including offset suction and air deflecting means for imparting a horizontal velocity component to the fibers in the direction of the moving wire. The patent reports more uniform distribution of fibers in the product.

U.S. Pat. No. 4,476,078 to Tao reports that air-laid webs are conventionally embossed either before or after the binder is applied and cured; each method having its advantages and drawbacks. Pre-embossing is reported to reduce line speed, while post-embossing lacks good embossing definition (col. 1, line 58–col. 2, line 13).

U.S. Pat. No. 4,612,231 of Bouchette et al. describes a patterned air-laid fibrous web of enhanced absorbency. According to the '231 patent, absorption rates are increased when at least about 40 percent of the imprinted area of the web is compressed (col. 2, lines 23–28).

Another method of increasing the absorbency of air-laid webs is disclosed in U.S. Pat. No. 5,128,082 to Makoui. The '082 patent describes making an absorbent structure by dry laying a fibrous web having incorporated therein a super-absorbent material such as poly(acrylic acid) or a salt thereof and apply a latex coating to at least one surface of the web.

Wave-like patterns have been employed to control fluid distribution in absorbent structures. U.S. Pat. Re 29,789 to Kolbach discloses a diaper with various emboss patterns. There is disclosed, for example, an emboss roll with circumferential wave bosses (46, FIG. 1) extending in the cross direction of a production line. The diapers have compressed channels 72 with a wavy line profile which function to direct fluid in the longitudinal direction. Col. 7, lines 60–63; column 8, lines 40–44.

U.S. Pat. No. 2,788,003 to Morin discloses a multi-layer diaper embossed with a wave-like pattern. The wave-like pattern is formed by embossing strips of the absorbent layer 17 against the facing sheet with a hot embossing tool. Column 3, lines 34–43. The embossed strips operate to convey fluid in the direction of the emboss lines. Column 4, lines 29–51.

SUMMARY OF INVENTION

There is provided in a first aspect of the present invention an absorbent sheet material including an air-laid fiber web provided with a functional emboss pattern directly applied to said air-laid web including a plurality of continuous sinuate compressed regions continuously extending in the machine direction of the air-laid web. The emboss pattern is operative to preferentially convey sorbed liquid along the continuous sinuate compressed regions throughout the sheet. In some embodiments the fiber web consists of cellulosic fiber and the sheet has a polymeric emulsion binder applied. In other embodiments, the fiber web includes both cellulosic pulp and synthetic fibers.

When synthetic fibers are employed, generally from about 5% to about 50% by weight of the fiber is synthetic fiber based on the combined weight of the synthetic fiber and cellulosic fiber. Typically, the fiber web includes from about 7.5% to 15% by weight synthetic fiber based on the weight of the synthetic and cellulosic fiber when synthetic fibers are employed. While any synthetic fiber may be included, typical fibers include rayon fibers, poly(ethylene) fibers, poly(propylene) fibers, poly(ethylene terephthalate) fibers, nylon fibers or mixtures thereof. Poly(ethylene) and poly(propylene) fibers are particularly preferred. So also, thermal bonding and bicomponent bonding fibers may be used. The air-laid web is typically bonded with a polymeric emulsion binder, however, a low melting polymer component such as a powder or fiber may be employed. Generally such polymeric components have a melting or softening point of less than about 250° F. and may be acrylics or olefins. Low melting fibers or bicomponent fibers with a low melting component such as poly(ethylene) may be used as a fibrous component for purposes of bonding the web if so desired.

The emboss pattern is preferably generally sinusoidal in shape and is applied in the machine direction during the manufacture of an air-laid absorbent sheet by way of an embossing roll with sinusoidal continuous radial bosses. It is most preferred to apply binder after the sheet is embossed with the sinuate pattern of the invention. In general, a polymeric emulsion binder is used in amounts from about 5 to about 30 percent by weight based on the weight of fiber and dry binder solution. From about 15 to about 25 percent by weight of a polymeric emulsion binder is typical based on the weight of fiber and dry binder solution.

The sinuate compressed regions are generally parallel to one another and have a width of from about 0.007 to about 0.60 inches. A width of from about 0.015 to about 0.35 inches is typical for the compressed regions, with a width of about 0.025 inches being a preferred value. The sinuate compressed regions are spaced at a distance of from about 0.1 to about 1.0 inch from one another with from about 0.2 to about 0.5 inches being typical. In one preferred embodiment, the compressed regions are spaced at a distance from one another of about 0.3 inches.

While the sinuate compacted regions are generally parallel, they may be either "in phase" or "out of phase" in the sense that when the crests and troughs are aligned in the cross direction as shown in FIG. 3, the pattern is termed "in phase". It is possible to manufacture the sheet wherein the pattern is completely out of phase in the sense a crest is adjacent a trough in the cross direction.

While the compressed regions may be prepared with a boss having any suitable relief height above the roll, a boss height of from about 0.015 inches to about 0.75 inches is generally employed. A boss height of from about 0.025 inches to about 0.05 inches is typical.

In order to provide for fluid transport in both the longitudinal and transverse directions, the sinuate pattern has a wave amplitude of from about 1 millimeter to about 8 millimeters; with from about 2 to about 5 millimeters being typical. While about 3.5 millimeters is a preferred amplitude. So also, the sinuate pattern generally has a repeat frequency of from about 0.5 to about 4.0 crests per inch; with from about 1 crest per inch to about 3 crests per inch being typical. A particularly preferred embodiment includes about 2 crests per inch.

There are numerous advantages realized with the absorbent sheet of the present invention. The use of a wavy line versus a straight line is advantageous for machine runnability—the stress of embossing is spread out over the surface. So also, the amount of the sheet densified is increased over straight lines or slightly wavy lines without increasing the thickness or width of the embossed region. Moreover, a machine direction continuous emboss is desirable for continuous fluid movement, preferably in applications such as feminine pads where distance in the cross or lateral direction is limited. Furthermore, direct densification of the web in air-laid products enhances web integrity. It should be noted that straight lines tend to weaken the web along the line, providing points of tear or perforation, while sinuate lines in accordance with the invention avoid these problems and that the aesthetics of a wavy line are generally more preferred by consumers than are those of straight lines.

It will be appreciated from the detailed description provided hereinafter that the use of narrow densified regions in accordance with the invention increase capillarity in these regions which, in turn, promotes liquid movement away from the insult point. In the absence of embossing, liquid spread tends to be circular which leads to product failure and leakage in products which are cross-direction, limited width products such as feminine pads or incontinence products. The functional sinuate pattern of the present invention spreads liquid in the machine direction to avoid saturation, without the need for a post-manufacture or multilayer embossing step.

The sheet of the invention may include a superabsorbent component such as poly(acrylic acid) or salts thereof. The superabsorbent polymer component may be in the form of powder, fiber, or applied as binder to the web fiber.

There is provided in another aspect of the present invention an absorbent structure including a planar absorbent core with a first and second surface including an air-laid fiber web provided with a functional emboss pattern directly applied to said air-laid web made up of a plurality of continuous sinuate compressed regions extending in the machine direction. The emboss pattern is operative to preferentially convey absorbed liquid along the continuous sinuate compressed region throughout the absorbent core. The absorbent structure additionally includes at least one of the following layers: (i) a permeable cover sheet disposed over the first surface of the planar absorbent core or (ii) a substantially impermeable backing disposed over the second surface of the planar absorbent core; or (iii) a nonwoven transfer layer adjacent the first surface of the planar absorbent core.

In a still further aspect of the invention, there is provided a method of making an embossed air-laid web including the steps of: (a) depositing a dry web of fibers on a foraminous support; (b) compacting the fiber web; (c) embossing the compacted web with an embossing roll provided with a plurality of sinuate bosses projecting radially around the circumference of the roll to provide the web with a functional emboss pattern including a plurality of continuous sinuate compressed regions extending in the machine direction of the air-laid web, the emboss pattern being operative to preferentially convey sorbed liquid along the plurality of continuous sinuate compressed regions of the web; and (d) bonding the web to produce the air-laid absorbent sheet material.

Preferably, the step of bonding the web is subsequent to the step of embossing the web, but embossing may be carried out subsequent to the step of bonding the web if so desired. Typically, the step of bonding the web includes (i) applying a polymeric emulsion binder to the web and (ii) curing the binder. Typically, the embossing roll is heated to a temperature of from about 100° F. to about 300° F., with from about 200° F. to about 260° F. being more usual.

The sheet according to the invention may be of various weights; generally from about 25 to about 400 lbs. per 3,000 square foot ream may be produced; however, from about 35 lbs. to about 150 lbs. per 3,000 square foot ream is typical of products of the present invention.

BRIEF DESCRIPTION OF THE DRAWINGS

The present invention is described in detail below with reference to the figures in which.

DETAILED DESCRIPTION

Figure 1:
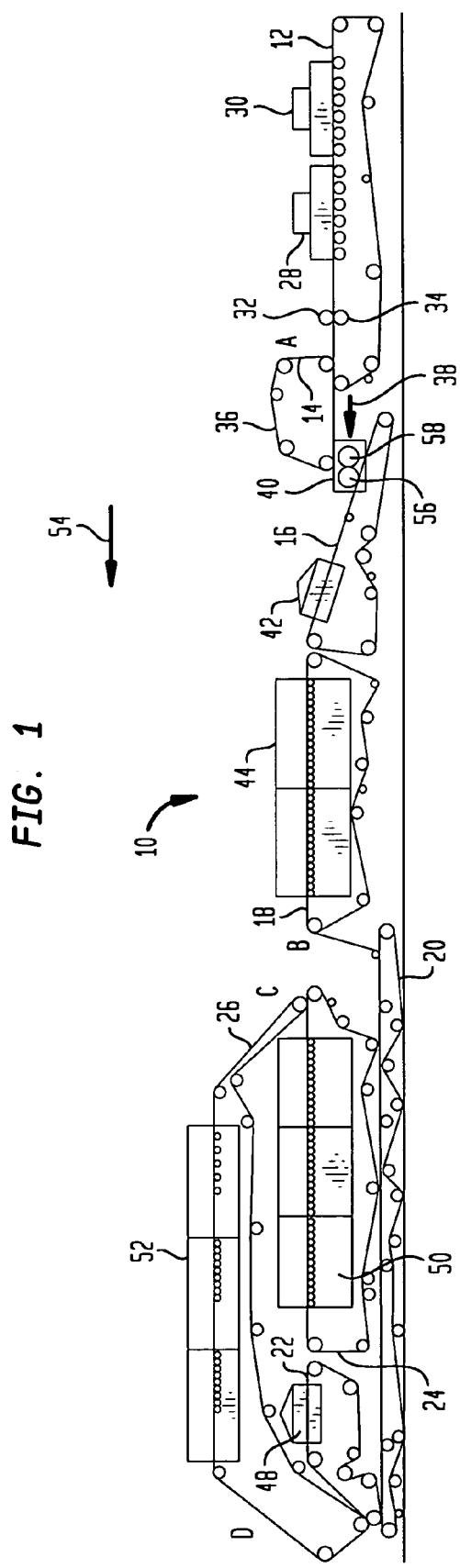
FIG. 1 is a schematic diagram generally illustrating the manufacture and embossing of an air-laid web.

The invention is described in detail below in various embodiments for purposes of illustration only. Modifications will be readily apparent to those of skill in the art within the spirit and scope of the invention which is set forth in the appended claims. The manufacture and embossing of air-laid sheet products is known in the art and is set forth in U.S. Pat. No. 4,437,917 to Tao et al.; U.S. Pat. Nos. 4,482,308 to Johnson; U.S. Pat. No. 4,476,078 to Tao; U.S. Pat. No. 4,612,231 of Bouchette et al.; and U.S. Pat. No. 5,128,082 to Makoui. The disclosure of these patents is incorporated herein by reference and will not be repeated for purposes of brevity; rather the present invention will be described in terms of differences from known products and processes for making them.

In general terms, the present invention is directed to an air-laid fiber web provided with a functional emboss pattern directly applied to said air-laid web which includes a plurality of generally parallel sinuate compressed regions in the web continuously extending in the machine direction. The emboss pattern, and more particularly, the compressed regions are operative to preferentially convey liquid away from a point of insult, as will be appreciated from the examples which follow. In preferred embodiments, the compressed regions are continuous in the sense that they are produced on a continuous line by a roll having a continuous radially projecting sinuate bosses about the entire circumference of the roll so that the compressed regions are co-extensive with the length of the sheet. The term continuous is also used herein to distinguish pin-like emboss patterns which do not provide for a continuous compressed region along the pattern.

Most commonly, the fiber web is formed primarily from cellulosic fibers (wood pulp), although synthetic fibers may be included as part of the fiber feedstock. When synthetic fibers are included, they are generally present from about 5 percent to about 50 percent by weight, based on the combined weight of synthetic and cellulosic fiber present. More typically when included, synthetic fibers are present from about 7.5 to about 15 weight percent based on the combined weight of the cellulosic and synthetic fibers.

Any suitable synthetic fiber may be included in the web. Fibers such as rayon, nylon, polyester, polyolefin and the like may be included to alter the strength of the product or act as a binder if so desired. Particularly preferred fibers include poly(ethylene terephthalate) fibers, poly(ethylene) fibers, and poly(propylene) fibers. Moreover, thermal bonding and bicomponent bonding fibers may be used as noted above.

The pattern of the invention is generally a collection of sinusoidal embossments, that is, of the form y=sineθ along the machine direction of the sheet. The embossments are typically applied using an embossing roll with continuous radially projecting circumferential bosses extending about its entire periphery as can be seen from FIG. 2. Air-laid webs are typically manufactured utilizing a polymeric emulsion binder material to impart structural integrity to the web. In order to impress a more permanent and better defined emboss pattern in accordance with the invention, it is preferred to emboss the sinuate pattern of the invention prior to the application of binder or bonding of the web by other means, such as thermal bonding. In some applications the use of emulsion binders and thermal binders may be combined. Generally, from about 5 percent to about 30 percent by weight of a polymeric emulsion binder is applied to the web based on the weight of the web and dry binder material; from about 15 to about 25 percent by weight of binder based on the weight of the fiber web and dry binder (i.e., solids content) is more typical.

The wave like, or sinuate, pattern generally consists of a plurality of parallel, wave like compressed areas. These parallel structures may be "in phase" in the cross direction, or, in the extreme may be "crest to trough" out of phase in the cross direction. It is believed that the "in phase" structures wherein the crests and troughs of adjacent compressed areas in the web line up in the cross direction are preferred.

The thickness of the lines of the pattern of the invention, actually the width of the compressed areas is generally from about 0.007 inches to about 0.60 inches; with from about 0.015 inches to about 0.35 inches being typical. A width of the compressed region of the web of about 0.025 inches is particularly preferred.

The compressed areas are generally spread from adjacent compressed areas at a distance of from about 0.1 inch to about 1 inch; with a separation between adjacent lines from about 0.2 inches to about 0.5 inches being typical. In a preferred embodiment, lines of the pattern are separated by a distance of about 0.3 inches.

The depth of the compacted areas does not necessarily approximate the relief height of the bosses on the embossing roll, depending primarily on the relationship of the boss height and the basis weight of the fibrous web. Thus, the depth of the pattern is generally specified herein by the relief height of the boss employed. Generally the sinuate embossed sheets are prepared from an embossing roll having a relief height of from about 0.005 inches to about 0.1 inch, with from about 0.015 to about 0.075 inches being typical. A boss relief height of from about 0.025 inches to about 0.050 inches is particularly preferred.

The sinuate compressed areas define wave amplitudes of generally from about 1 to about 8 millimeters, whereas from about 2 millimeters to about 5 millimeters is typical. In a preferred embodiment, the wave pattern has a wave amplitude of about 3.5 millimeters.

The pattern also has a repeat frequency in the machine direction of generally from about 0.5 to about 4 crests per inch. From about 1 to about 3 crests per inch is typical, while a repeat frequency of about 2 crests per inch is suitable for a preferred embodiment.

The sheet of the invention optionally includes a superabsorbent polymer component. Such polymers are generally organic polymers with an acid or acid salt as a sidechain, typically a carboxylic acid sidechain or a sulfonic acid sidechain including salts of the sodium, potassium or calcium form, for example. The materials are available from Dow Corporation, Midland, Mich., or BASF Corporation, Mount Olive, N.J. Particularly preferred materials are poly (acrylic acid) superabsorbent polymer. The superabsorbent component can be added to the web during the step of depositing the fibers on the foraminous forming wire in the form of powder, granules, fiber or the like or may be added to a formed web as part of the binder or applied simultaneously with the binder as hereinafter described.

The absorbent sheet material of the invention is particularly useful as absorbent core material for a feminine pad or an incontinence pad. An absorbent structure in accordance with the invention includes a planar absorbent core with a first and second surface including an air-laid fiber web provided with a functional emboss pattern directly applied to said air-laid web including a plurality of continuous sinuate compressed regions in the web extending in the machine direction. The emboss pattern is operative to preferentially convey sorbed liquid along the continuous sinuate compressed regions. Typically, the absorbent core is covered on one surface by a permeable cover sheet (permeable in the sense that liquid readily penetrates to the core), and on the other surface by a polymer film poly backing material which is substantially impermeable to liquids. Such a poly film backing may include, for example, a perforated poly(ethylene) or poly(propylene) membrane. The absorbent structure further optionally includes a nonwoven transfer layer between the cover layer and the absorbent core. The core may also optionally be folded about a superabsorbent structure of acrylic acid polymer or its salts if so desired in order to provide additional sorbtion capacity to the structure.

In general, the embossed sheet of the present invention is made by depositing a dry web of fibers on a foraminous support; compacting the fiber web; embossing the compacted web with an embossing roll provided with a plurality of sinuate bosses projecting radially about the roll to provide a functional emboss pattern including a plurality of continuous sinuate compressed regions extending in the machine direction of the web; and bonding the web. The step of applying binder is preferably carried out after the sheet is embossed with a roll heated to a temperature of from about 100° F. to about 300° F. Typically, the embossing roll is heated to a temperature of from about 200° F. to about 260° F. The absorbent air-laid absorbent sheet generally has a basis weight of from about 25 to about 400 lbs. per 3,000 square foot ream, with from about 40 lbs. to about 80 lbs. per square foot ream being typical.

A continuous air-laid web in accordance with the invention is manufactured on a high speed line as are well known in the art. There is shown in FIG. 1 such a line, known as an air-laid machine available from M&J or Dan Web Forming of Denmark. Web processing is typically pneumatically assisted as is well known in the art.

Apparatus 10 of FIG. 1 includes conveyor wires (or fabrics) 12, 14, 16, 18, 20, 22, 24 and 26 which are foraminous (that is, porous) supports for the product as it is continuously manufactured in the various steps. The foraminous supports may be metal screens or porous fabric as so desired. Wire 12, the forming wire, is located underneath a pair of fiber distributors 28, 30 which deposit a dry fibrous web onto forming wire 12, typically under suction on the underside of the wire. The web is then conveyed to a pair of compacting rolls 32, 34 which are smooth surfaced and only slightly loaded in order to compact the web and provide it with some modicum of strength. If so desired, a pair of embossing rolls (not shown) could be disposed as indicated at A if it were desired to emboss the web at this point. At A, it would be convenient to perform roll to wire embossing, that is, employ a patterned roll as the top roll and utilize a support roll under the wire. Embossing rolls are typically heavily loaded or biased towards each other and a patterned roll is preferably heated in order to impress a pattern on the fabric.

After compaction, the web is transferred to a web transfer section indicated at 36, where the web is transferred upwardly onto wire 14 as indicated by arrow 38 and eventually downwardly to an emboss section 40. At section 40 it is convenient to employ roll to roll embossing, as will be appreciated by those of skill in the art, before the web is transferred to third conveyor wire 16. Wire 16 transports the web to a spray cabin 42 where a binder, typically a latex binder is sprayed onto the web. Thereafter, the web is transferred to the fourth conveyer wire 18 and fed to a dryer. Typically the first application of binder is about 5–10 weight percent based on the weight of dry fiber and dry binder.

After drying, it would be convenient to emboss the continuous web at B with roll to roll embossing; however, it has been found that embossing in according with the present invention is generally more effective prior to the application of binder.

The web is transferred from wire 18 to wire 20 where the web is conveyed to wire 22 which transports the web to spray cabin 48 where binder is supplied to the side of web which was adjacent the wire in spray cabin 42. During the second application of binder, typically about 5–10 weight percent binder is applied to the web based on the weight of the dry fiber and dry binder material. It should be noted that while fiber is referred to as "dry" it will be understood that fiber as supplied to the manufacturing process includes a few percent moisture.

Following the second application of binder the web is transferred to wire 24 and fed to dryer 50. Thereafter, the web is transferred to wire 26. At the transfer point C, it is convenient to emboss the web with roll to roll or roll to wire embossing as is the case at A.

Wire 26 conveys the web to a cure oven 52 for curing and finishing the web, which may be embossed at location D with roll to roll or roll to wire embossing if so desired. The embossing process of the present invention is most preferably carried out at location A, or at emboss station 40 prior to the application of binder. However, the sinuate pattern could also be applied at location B, C or D, or even after initial manufacture so long as the pattern is applied directly to the web.

Figure 2:
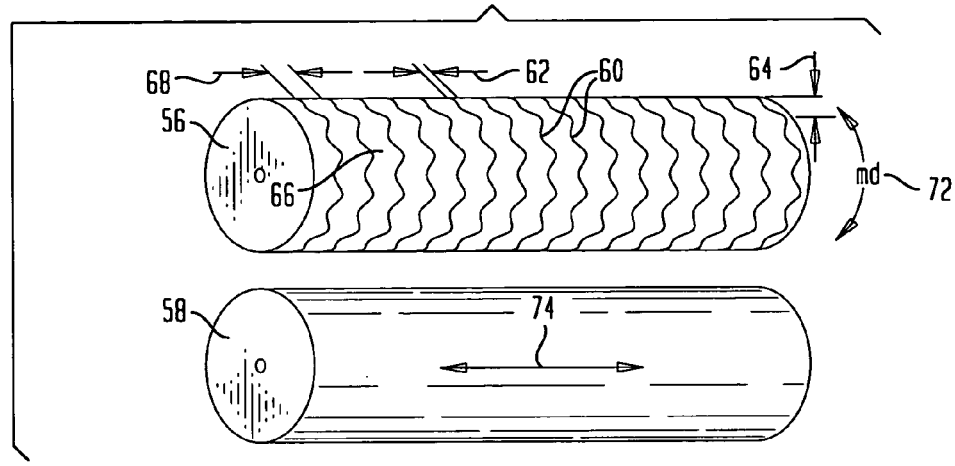
FIG. 2 is a detail of the schematic diagram of FIG. 1 showing in perspective embossing nip rolls utilized in accordance with the present invention on an apparatus such as is shown in FIG. 1.

The emboss rolls are located with their longitudinal axes perpendicular to the machine direction generally indicated by arrow 54 in FIG. 1, and may be located as rolls 56, 58 which are also depicted in FIG. 2. It shall be appreciated in connection with FIGS. 1 and 2 that the radially projecting sinuate bosses of roll 56 extend around the entire circumference of the roll and are aligned in the machine direction, or the direction of travel of the web as it is produced. In this regard, arrow 54 is only a general indication of machine direction, but it should be readily apparent that the sinuate pattern extends continuously along the continuous web in the machine direction from the point of application of the emboss. The sinuate emboss pattern on the roll and on the sheet is thus in the direction perpendicular to the longitudinal axis of the emboss roll shown in FIG. 2.

There is shown in FIG. 2 diagramatically the emboss roll 56, 58 of FIG. 1. Patterned roll 56 is typically steel or may be hard rubber, while smooth emboss roll 58 may be rubber or steel, soft or hardened material. Roll 56 is provided with a plurality of raised sinosoidal bosses 60 having a typical width 62 of 0.025 inches, a relief height 64 of typically from about 0.025 to about 0.05 inches above the surface 66 of the roll between bosses. The bosses are separated by a distance 68 of 0.3 inches, have a wave amplitude of approximately 3.5 mm and a repeat frequency of approximately 2 crests per inch which will be better appreciated from FIGS. 3 and 4.

Figure 3:
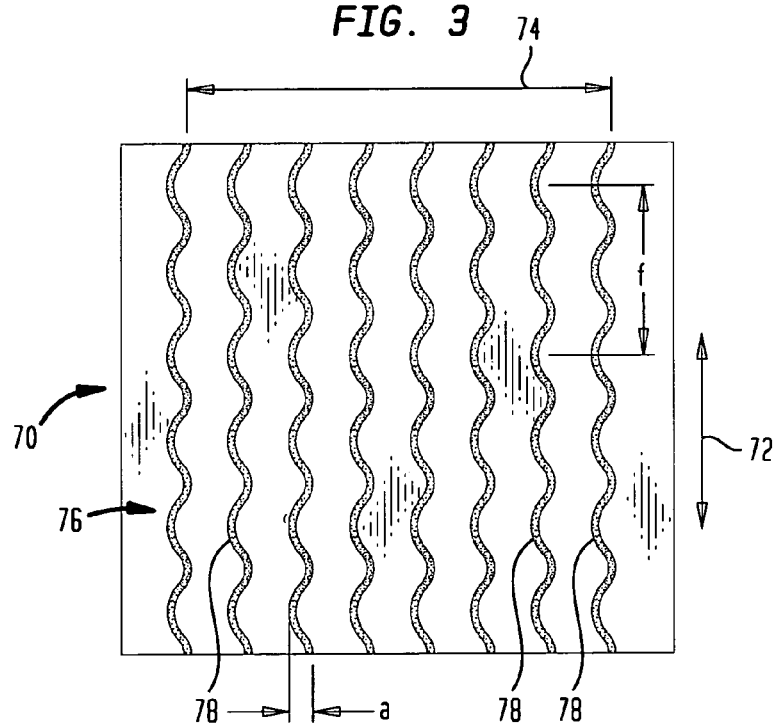
FIG. 3 is a top plan view illustrating a section of a continuous absorbent sheet manufactured in accordance with the present invention.
Figure 4:
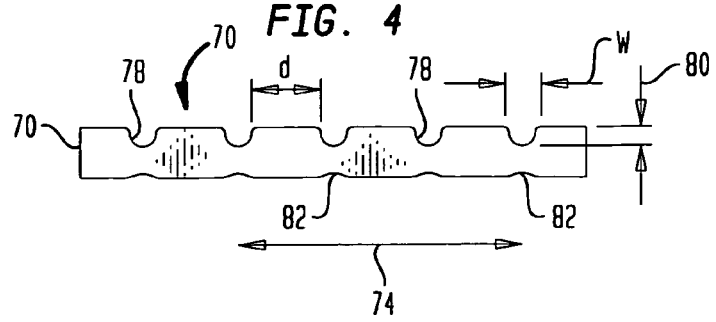
FIG. 4 is a view in elevation and section of the absorbent sheet of FIG. 3.

In operation, rolls 56, 58 are loaded against one another under pressure with only the fibrous web separating them to produce a continuous sheet product, a section of which is depicted in top plan view in FIG. 3 and in elevation in FIG. 4. It should be appreciated that bosses 60 are radially projecting and extend around the entire circumference of roll 56 to produce the continuous compressed regions shown in sheet 70 of FIGS. 3 and 4.

The machine direction, 72, of apparatus 10 is shown in FIG. 3 and corresponds generally to direction 54 as noted above, while the cross direction, 74, is parallel to the axis of the rolls and perpendicular to the direction of the sinosoidal pattern 76.

Roll 56 is operative to imprint pattern 76 on sheet 70 as shown in FIGS. 3 and 4. Sheet 70 has a plurality of compressed sinuate regions 78 with shapes corresponding to bosses 60 on roll 56. Thus, compressed regions 78 have a width, w, of about 0.025 inches, are separated by a distance, d, of about 0.3 inches, a wave amplitude (peak to trough), a, of about 3.5 millimeters and a repeat frequency, f, of approximately 2 crests per inch. These dimensions ordinarily correspond quite closely to the bosses on roll 56. It is always permissible in any event to define the dimensions recited herein for the sheet as those of the bosses and the roll since the roll is a more robust material. This is particularly true with respect to the depth or the embossments on the air-laid web, since it may not correspond to the relief height of the bosses on roll 56, depending upon the relationship between the boss height and basis weight of the web. Thus, the depth 80 shown on FIG. 4 is preferably defined in terms of relief height 64 as noted with particularity herein.

It should be noted on FIG. 4 that although roll 58 is unpatterned, there are slight depressions 82 in the lower surface of the inventive sheet due to compaction. Typically, these depressions are only 10–20% of the depth 80 of compacted regions 78 (FIG. 4). Moreover, it should be apparent that it is preferred the sinuate pattern repeats over the entire continuous sheet in both the machine direction and the cross direction in the sense that adjacent lines are preferably imprinted over the entire sheet.

The sinosoidal pattern of the invention is illustrated "in phase" in FIG. 3, that is the peaks and troughs of adjacent lines are aligned in the cross direction. It is likewise possible to apply the pattern "out of phase" wherein peaks and troughs of adjacent lines are offset in the cross direction if so desired.

The absorbent sheet of the present invention is particularly useful in absorbent structures such as feminine pads, incontinence pads, and surgical drapes due to its unique fluid distribution properties.

Figure 5:
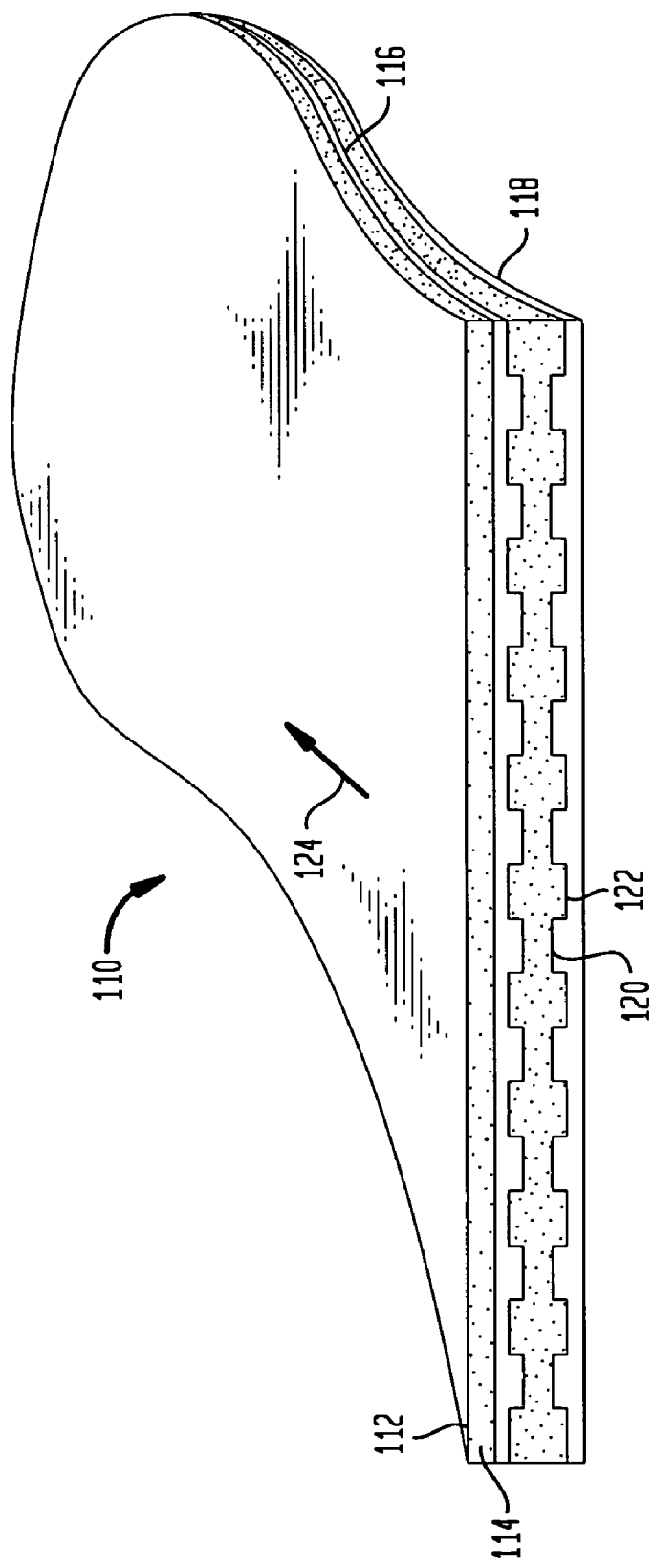
FIG. 5 is a schematic illustration of an absorbent pad incorporating the absorbent sheet of FIGS. 3 and 4.

There is shown in FIG. 5 a schematic diagram of a feminine pad utilizing the sheet of the present invention. Pad 110 includes generally a cover layer 112, a nonwoven transfer layer 114, an air-laid absorbent core 116 and a polymer film backing 118. Layer 112 is generally formed of a synthetic fiber web, while nonwoven transfer layer 114 is typically a highly permeable sheet of thermally bonded nonwoven bicomponent poly(ethylene terephthalate) fibers surface treated for wettability. Film 118 is typically a poly(ethylene) or poly(propylene) sheet which may be provided with pores for breathability.

Core 116 is either a single layer or a C-folded structure, that is, end to end folded sheet of the sinuate embossed air-laid fabric of the invention and may include a superabsorbent polymer or fibrous structure if so desired. A "C" folded structure is folded so that a double layer with one seam is formed. Thus, where compacted regions of the sheet meet as shown diagramatically at 120, the effect of compaction is doubled. Likewise, the lower density regions between embosses will form a much thicker structure when one compacted region meets another as indicated at 122. In FIG. 5, it should be appreciated that the sinuate pattern of the core extends generally in the longitudinal direction 124 of the pad, since it is desirable to direct fluid in the direction when the pad is in use.

EXAMPLES 1–3 AND COMPARATIVE EXAMPLE A

Three samples were prepared having the general dimensions and embossment pattern described in connection with FIGS. 3 and 4, the only difference being the width of the emboss pattern. The first sample (Example 1) had a compressed region width of 0.025 inches, the second (Example 2) a compressed region width of 0.050 inches and the third (Example 3) had a compressed region width of 0.075 inches. A fourth sample (Comparative Example A) was prepared without an embossment pattern. All four samples were insulted with 1 milliliter of colored 1% saline through a 1" diameter hole in a Lucite block and the progress of the fluid in the sheet was measured as a function of time in the machine direction.

In Table 1, the length of fluid progress in the machine direction was the observed maximum wet-out along the length of the emboss pattern in the machine direction (or just the machine direction in the case of Comparative Example A), while the oval in the center was the area of solid color about the point of insult. In general, the area of solid color was elliptical in shape; the length of the major and minor axes being recorded in Table 1.

Figure 6:
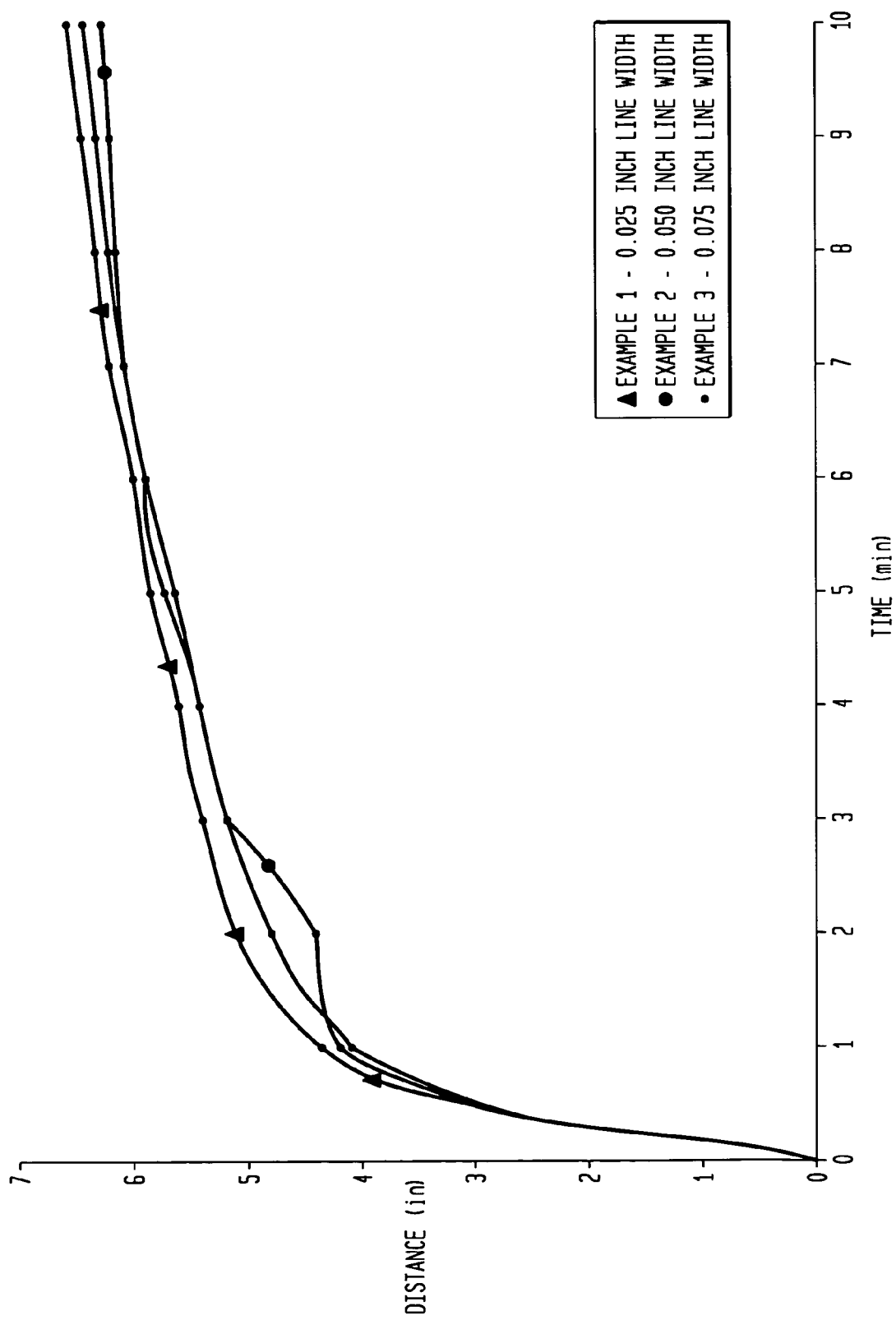
FIG. 6 is a plot of fluid distribution in the machine direction vs. time for sheets of the present invention.

Results appear in Table 1 below and are presented graphically in FIG. 6 for Examples 1–3.

TABLE I

Sheet Performance vs. Time

| | Length of Fluid Progress in Machine Direction (inches) | | | Comparative |
|---|---|---|---|---|
| Time (min.) | Example 1 | Example 2 | Example 3 | Example A |
| 1 | 4 5/16 | 4 3/16 | 4 2/16 | 2 3/16 |
| 2 | 5 2/16 | 4 7/16 | 4 13/16 | 2 7/16 |
| 3 | 5 3/16 | 5 3/16 | 5 3/16 | 2 7/16 |
| 4 | 5 10/16 | 5 7/16 | 5 7/16 | 2 7/16 |
| 5 | 5 14/16 | 5 11/16 | 5 12/16 | 2 7/16 |
| 6 | 6 1/6 | 5 15/16 | 5 15/16 | 2 7/16 |
| 7 | 6 4/16 | 6 2/16 | 6 2/16 | 2 7/16 |
| 8 | 6 6/16 | 6 3/16 | 6 4/16 | 2 7/16 |
| 9 | 6 8/16 | 6 4/16 | 6 6/16 | 2 7/16 |
| 10 | 6 10/16 | 6 5/16 | 6 8/16 | 2 7/16 |
| Oval in center* | 2 4/16 L × 1 10/16 W | 2 L × 1 12/16 W | 2 4/16 L × 2 W | 1 13/16 L × 1 8/16 W |

*solid color stain

From the foregoing it is observed that: (a) when the sheet is unembossed, fluid distribution is only slightly preferential to the machine direction) making the fluid distribution pattern mostly circular; (b) fluid distribution in an oval pattern is the effect of wavy line emboss. The area of wet out is significantly increased over that of an unembossed sheet (~2×).

It can also be seen that (a) when comparing between the three pattern types, in the embossed area, the pattern of Example 1 moves the fluid in the MD farther and faster than the other wider lines versions (~5–10% after 2 min.); and (b) the pattern of Example 1 has the longest and narrowest oval pattern of all three versions (length 0–12% increase, width 7–19% decrease).

EXAMPLES 4–9

A mock-up pad was prepared by "C" folding a core of absorbent sheet of Examples 1 and 3 about a strip of superabsorbent material and covering the structure with a nonwoven layer and a cover layer as discussed above in connection with FIG. 5. The pads were insulted with 10 ml, 5 ml, and 2 mil of 1% colored saline solution through a 1" diameter hole in a Lucite block and the pattern of the fluid on the sheet was measured after 10 minutes. Results appear in Table 2 below.

The reported "oval" values in Table 2 are the observed major and minor axes of the oval stain on the cover sheet of the mock-up pad, while the reported "wavy" values are the lengths of fluid travel along the embossed areas measured after dissection of the pad.

TABLE 2

| Fluid Distribution Within Pad | | |
| --- | --- | --- |
| 10 ml | 5 ml | 2 ml |
| Material of Example 1; (L (inches) × W (inches)) | | |
| Oval 3 L × 2²⁄₁₆ W | 2²⁄₁₆ L × 1¹²⁄₁₆ W | 1⁷⁄₁₆ L × 1⁷⁄₁₆ W |
| Wavy 8 L × 2²⁄₁₆ W | 6⁸⁄₁₆ L × 1¹⁵⁄₁₆ W | 4¹⁵⁄₁₆ L × 1⁷⁄₁₆ W |
| Material of Example 3; L (inches) × W (inches) | | |
| Oval 3 L × 2²⁄₁₆ W | 2³⁄₁₆ L × 2 W | 1⁸⁄₁₆ L × 1¹¹⁄₁₆ W |
| Wavy 7¹⁵⁄₁₆ L × 2²⁄₁₆ W | 6³⁄₁₆ L × 2²⁄₁₆ | 4¹⁰⁄₁₆ L × 1¹¹⁄₁₆ W |

Three criteria were measured: length and width of oval, and length traveled on embossed area. The desired effect is longer and narrower ovals with longer wetted out embossed area. On a two to one basis the pattern of Example 1 beat the Example 3 pattern for the above listed criteria. This effect is dramatized at an insult level of 2 mL (A decrease in oval width of ~15% and ~equal for oval length, and an ~7% increase in length on embossed area traveled). Similar but less dramatic effects were noticed up to a 10 ml insult.

While the invention has been described in detail in its various features, embodiments and applications, various modifications to those features, embodiments and applications within the spirit and scope of the present invention will be apparent to those of skill in the art. The invention is not intended to be limited in any way by the foregoing description which is merely for purposes of illustration and exemplification.

What is claimed is:

1. An absorbent sheet material consisting of an air-laid fiber web having a machine direction and provided with a permanent functional emboss pattern directly applied to said air-laid web by way of an embossing roll during manufacture thereof, the pattern comprising a plurality of continuous sinuate mechanically compressed regions continuously extending in the machine direction of said air-laid web, said emboss pattern being operative to preferentially convey sorbed liquid along said continuous sinuate compressed regions throughout said sheet, wherein said plurality of continuous sinuate compressed regions have a width of from about 0.007 inches to about 0.60 inches, the compressed regions being configured to enhance migration of sorbed liquid in the machine direction as compared with a same sheet without an embossment pattern.

2. The absorbent sheet material according to claim 1, wherein said fiber web consists of cellulosic fibers.

3. The absorbent sheet material according to claim 1, wherein said fiber web comprises synthetic fibers and cellulosic fibers.

4. The absorbent sheet material according to claim 3, wherein said fiber web comprises from about 5% to about 50% by weight of synthetic fiber based on the combined weight of synthetic and cellulosic fiber.

5. The absorbent sheet material according to claim 4, wherein said fiber web comprises from about 7.5% to about 15% by weight of synthetic fiber based on the combined weight of synthetic and cellulosic fiber.

6. The absorbent sheet material according to claim 4, wherein said synthetic fiber comprises a thermally bondable fiber selected from the group consisting of low melting fibers and bicomponent fibers with a low melting component.

7. The absorbent sheet material according to claim 6, wherein said low melting fibers and said low melting component of said bicomponent fibers comprise polyethylene.

8. The absorbent sheet material according to claim 3, wherein said synthetic fibers are selected form the group consisting of: rayon fibers, poly(ethylene) fibers, poly(propylene) fibers, poly(ethylene terephthalate) fibers, nylon fibers and mixtures thereof.

9. The absorbent sheet material according to claim 8, wherein said synthetic fibers are poly(ethylene) fibers or poly(propylene) fibers.

10. The absorbent sheet material according to claim 1, wherein said functional emboss pattern is sinusoidal.

11. The absorbent sheet material according to claim 10, wherein said pattern is applied in the machine direction of an air-laid web by an embossing roll with a plurality of continuous radial sinusoidal bosses extending about its circumference.

12. The absorbent sheet material according to claim 1, wherein said emboss pattern is applied to said sheet prior to the application of binder to said sheet.

13. The absorbent sheet material according to claim 1, wherein said emboss pattern is applied to said sheet after the application of binder to said sheet.

14. The absorbent sheet material according to claim 1, wherein from about 5 to about 30 percent by weight of a polymeric emulsion binder is applied to said absorbent sheet material based on the weight of fiber and polymeric binder material on a dry basis.

15. The absorbent sheet material according to claim 1, wherein from about 15 to about 25 percent by weight of the polymeric emulsion binder is applied to said absorbent sheet material based on the weight of fiber and polymeric binder material on a dry basis.

16. The absorbent sheet material according to claim 1, wherein said plurality of continuous sinuate compressed regions are parallel.

17. The absorbent sheet material according to claim 16, wherein the sheet has a machine direction and a cross direction and the sinuate compressed regions each have troughs and crests and wherein further the troughs and crests of said sinuate compressed regions are aligned in the cross direction of the sheet such that the troughs and crests are in phase.

18. The absorbent sheet material according to claim 16, wherein the sheet has a machine direction and a cross direction and the sinuate compressed regions each have troughs and crests and wherein further the troughs and crests of said sinuate compressed regions are offset in the cross direction of the sheet such that the troughs and crests are out of phase.

19. The absorbent sheet material according to claim 1, wherein said plurality of sinuate compressed regions have a width of from about 0.015 inches to about 0.35 inches.

20. The absorbent sheet material according to claim 19, wherein said plurality of sinuate compressed regions have a width of about 0.025 inches.

21. The absorbent sheet material according to claim 1, wherein said plurality of sinuate compressed regions are spaced at a distance from one another of from about 0.1 inches to about 1.0 inch.

22. The absorbent sheet material according to claim 21, wherein said plurality of sinuate compressed regions are spaced at a distance from one another from about 0.2 inches to about 0.5 inches.

23. The absorbent sheet material according to claim 22, wherein said plurality of sinuate compressed regions are spaced at a distance from one another of about 0.3 inches.

24. The absorbent sheet material according to claim 1, wherein said plurality of sinuate compressed regions are prepared employing an embossing roll with a plurality of continuous radial bosses extending about its circumference, the radial bosses having a height of from about 0.015 inches to about 0.1 inch.

25. The absorbent sheet material according to claim 24, wherein said plurality of sinuate compressed regions are prepared employing an embossing roll with a plurality of continuous radial bosses extending about its circumference, the radial bosses having a height of from about 0.015 inches to about 0.075 inches.

26. The absorbent sheet material according to claim 25, wherein said plurality of sinuate compressed regions are prepared employing a continuous sinuate boss having a height of from about 0.025 inches to about 0.050 inches.

27. The absorbent sheet material according to claim 1, wherein said plurality of sinuate compressed regions have a wave amplitude of from about 1 millimeter to about 9 millimeters.

28. The absorbent sheet material according to claim 27, wherein said plurality of sinuate compressed regions have a wave amplitude of from about 2 millimeters to about 5 millimeters.

29. The absorbent sheet material according to claim 28, wherein said plurality of sinuate compressed regions have a wave amplitude of about 3.5 millimeters.

30. The absorbent sheet material according to claim 1, wherein said plurality of sinuate compressed regions have a repeat frequency of from about 0.5 to about 4 crests per inch.

31. The absorbent sheet material according to claim 30, wherein said plurality of sinuate compressed regions have repeat frequency of from about 1 to about 3 crests per inch.

32. The absorbent sheet material according to claim 31, wherein said plurality of sinuate compressed regions have a repeat frequency of about 2 crests per inch.

33. The absorbent sheet material according to claim 1, wherein said sheet material includes a superabsorbent polymer component.

34. The absorbent sheet material according to claim 33, wherein said absorbent sheet material is selected from the group consisting of superabsorbent powder, superabsorbent fiber and superabsorbent binder material.

35. An absorbent structure comprising:
(a) a planar absorbent core with a first and second planar surface including an air-laid fiber web having a machine direction and provided with a permanent functional emboss pattern directly applied to said air-laid web by way of an embossing roll during manufacture thereof, the pattern comprising a plurality of continuous sinuate mechanically compressed regions continuously extending in the machine direction of said air-laid web, said emboss pattern being operative to preferentially convey sorbed liquid along said continuous sinuate compressed regions throughout said absorbent core, wherein from about 5 to about 30 percent by weight of a polymeric emulsion binder is applied to said absorbent core based on the weight of fiber and polymeric binder material on a dry basis; and
(b) at least one of the following optional components:
  (i) a permeable cover sheet juxtaposed over said first planar surface of said planar absorbent core; or
  (ii) a substantially impermeable backing juxtaposed over said second planar surface of said planar absorbent core; or
  (iii) a non-woven transfer layer adjacent said first planar surface of said planar absorbent core.

36. An absorbent sheet material comprising an air-laid fiber web having a machine direction and provided with a functional permanent emboss pattern directly applied to said air-laid web by way of an embossing roll during manufacture thereof the pattern comprising a plurality of continuous sinuate mechanically compressed regions having a width of from about 0.007 inches to about 0.6 inches, the compressed regions having an embossed depth on one side of the sheet due to contact with bosses on an embossing roll as well as corresponding depressions on the opposite side of the sheet such that the compressed regions are manifested on both sides of the sheet and wherein the sinuate compressed regions continuously extend in the machine direction of said air-laid web, said emboss pattern being operative to preferentially convey sorbed liquid along said continuous sinuate compressed regions.

37. An absorbent sheet material consisting of an air-laid fiber web having a machine direction and provided with a functional permanent emboss pattern directly applied to said air-laid web by way of an embossing roll during manufacture thereof, the pattern comprising a plurality of continuous sinuate mechanically compressed regions continuously extending in the machine direction of said air-laid web, said emboss pattern being operative to convey sorbed liquid along said continuous sinuate compressed regions, wherein a 10 ml insult of 1% saline applied to the sheet through a 1 inch diameter template progresses at least about 4 inches in the machine direction in less than 5 minutes.

38. An absorbent sheet material consisting of an air-laid fiber web having a machine direction and provided with a functional permanent emboss pattern directly applied to said air-laid web by way of an embossing roll during manufacture thereof, the pattern comprising a plurality of continuous sinuate mechanically compressed regions continuously extending in the machine direction of said air-laid web, wherein from about 5 to about 30 percent by weight of a polymeric emulsion binder is applied to said absorbent sheet material based on the weight of fiber and polymeric binder material on a dry basis; and said emboss pattern being operative to preferentially convey sorbed liquid along said continuous sinuate compressed regions throughout said sheet, wherein said plurality of continuous sinuate compressed regions have a width of from about 0.007 inches to about 0.60 inches, the compressed regions being configured to enhance migration of sorbed liquid in the machine direction as compared with a same sheet without an embossment pattern, and wherein a 10 ml insult of 1% saline applied to the sheet through a 1 inch diameter template progresses at least about 4 inches in the machine direction in less than 5 minutes.

39. An absorbent sheet material consisting of an air-laid fiber web having a machine direction and provided with a permanent functional emboss pattern directly applied to said air-laid web by way of an embossing roll during manufacture thereof, the pattern comprising a plurality of continuous sinuate mechanically compressed regions continuously extending in the machine direction of said air-laid web, said emboss pattern being operative to preferentially convey sorbed liquid along said continuous sinuate compressed regions throughout said sheet, wherein said plurality of continuous sinuate compressed regions have a width of from about 0.007 inches to about 0.60 inches, the compressed regions being configured to enhance migration of sorbed liquid in the machine direction as compared with a same sheet without an embossment pattern and wherein the sheet material is of generally uniform thickness other than the emboss pattern.

* * * * *

UNITED STATES PATENT AND TRADEMARK OFFICE
CERTIFICATE OF CORRECTION

PATENT NO.        : 7,195,810 B1
APPLICATION NO.   : 09/553928
DATED             : March 27, 2007
INVENTOR(S)       : Bradley G. Schmidt et al.

It is certified that error appears in the above-identified patent and that said Letters Patent is hereby corrected as shown below:

In Column 2, line 16, delete "apply" and insert --applying--;
In Column 4, line 22, insert --;-- after "core";
In Column 5, line 34, delete the 3rd instance of "a";
In Column 7, line 35, insert --3,000-- before "square";
In Column 8, line 9, delete "according" and insert --accordance--;
In Column 10, line 2, delete the 2nd instance of "the" and insert --that--;
In Table 1 (Column 10), line 34, delete "I" and insert --1--;
In Table 1 (Column 10), line 45, delete "6 1/6" and insert --6 1/16--;
In Column 10, line 56, delete ")";
In Column 11, line 8, delete "mil" and insert --ml--;
In Table 2 (Column 11), line 22, delete "(" before "L";
In Table 2 (Column 11), line 29, insert --W-- after "2 4/16";
In Column 11, line 36, delete "mL" and insert --ml--; and
In Column 12, line 22, delete "form" and insert --from--.

Signed and Sealed this

Third Day of June, 2008

JON W. DUDAS
*Director of the United States Patent and Trademark Office*